United States Patent
Stamler et al.

(10) Patent No.: US 9,086,411 B2
(45) Date of Patent: Jul. 21, 2015

(54) RESIN ASSISTED CAPTURE OF CYSTEINE-MODIFIED PROTEINS/PEPTIDES AND DETERMINATION OF PRESENCE AND LOCATION OF MODIFICATION

(75) Inventors: Jonathan Stamler, Chapel Hill, NC (US); Michael Forrester, Durham, NC (US); Matthew Foster, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 535 days.

(21) Appl. No.: 12/745,005

(22) PCT Filed: Dec. 10, 2008

(86) PCT No.: PCT/US2008/013538
§ 371 (c)(1),
(2), (4) Date: Sep. 9, 2010

(87) PCT Pub. No.: WO2009/085106
PCT Pub. Date: Jul. 9, 2009

(65) Prior Publication Data
US 2011/0008811 A1    Jan. 13, 2011

Related U.S. Application Data

(60) Provisional application No. 61/009,162, filed on Dec. 27, 2007.

(51) Int. Cl.
| | | |
|---|---|---|
| *G01N 33/68* | (2006.01) | |
| *C07K 1/16* | (2006.01) | |
| *G01N 33/548* | (2006.01) | |
| *C07K 1/107* | (2006.01) | |
| *C07K 1/113* | (2006.01) | |
| *C07K 1/13* | (2006.01) | |
| *C07K 1/22* | (2006.01) | |
| *C08H 1/00* | (2006.01) | |
| *G01N 33/543* | (2006.01) | |

(52) U.S. Cl.
CPC .......... *G01N 33/548* (2013.01); *C07K 1/1072* (2013.01); *C07K 1/1133* (2013.01); *C07K 1/13* (2013.01); *C07K 1/22* (2013.01); *C08H 1/00* (2013.01); *G01N 33/54353* (2013.01); *G01N 33/6842* (2013.01)

(58) Field of Classification Search
None
See application file for complete search history.

(56) References Cited

U.S. PATENT DOCUMENTS

| | | | | |
|---|---|---|---|---|
| 4,886,755 A | * | 12/1989 | Ngo | 435/183 |
| 5,807,997 A | * | 9/1998 | Batista | 530/362 |
| 5,824,669 A | * | 10/1998 | Garvey et al. | 514/174 |
| 7,179,613 B2 | * | 2/2007 | Rizzo et al. | 435/15 |
| 7,622,273 B2 | * | 11/2009 | Gibbs | 435/23 |
| 7,687,611 B2 | * | 3/2010 | Kapteyn et al. | 530/412 |
| 7,989,594 B2 | * | 8/2011 | Humphreys et al. | 530/387.1 |
| 2002/0132990 A1 | | 9/2002 | Huston et al. | |
| 2005/0090651 A1 | | 4/2005 | Smith et al. | |
| 2005/0095661 A1 | | 5/2005 | Hamon et al. | |
| 2006/0199280 A1 | | 9/2006 | Bar-Or et al. | |

FOREIGN PATENT DOCUMENTS

| | | |
|---|---|---|
| CN | 101089608 A | 6/2006 |
| WO | WO 2006/094185 A2 | 9/2006 |

* cited by examiner

*Primary Examiner* — Kade Ariani
*Assistant Examiner* — Charles Zoltan Constantine
(74) *Attorney, Agent, or Firm* — Bacon & Thomas, PLLC

(57) ABSTRACT

A resin connected by amide bond to pyridyl sulfide or methylthiosulfonate can be conjugated to a post traditionally modified protein/peptide to allow determination of presence and kind and optionally location of cysteine modification(s).

4 Claims, No Drawings

RESIN ASSISTED CAPTURE OF CYSTEINE-MODIFIED PROTEINS/PEPTIDES AND DETERMINATION OF PRESENCE AND LOCATION OF MODIFICATION

CROSS-REFERENCE TO RELATED APPLICATIONS

This application claims the benefit of U.S. Provisional Application No. 61/009,162, filed Dec. 27, 2007, the whole of which is incorporated herein by reference.

TECHNICAL FIELD

This invention is directed to a chemical entity for the efficient solid phase immobilization of modified protein/peptide cysteine residues, a method for synthesis thereof, and methods involving immobilization of modified protein/peptide cysteine residues.

BACKGROUND OF THE INVENTION

Dysregulation of specific protein modifications in cells and/or tissues has been implicated in a wide range of pathophysiological conditions from neurodegeneration to heart failure. Progress in elucidating the role of these specific protein modifications in health and disease requires methods for identification and quantitation of the specific protein modifications, as well as the specific amino acids residues that are targets of protein modification.

For example, nitric oxide exerts a ubiquitous influence on cellular signaling, effected through the coordinated S-nitrosylation/denitrosylation of critical cysteine residues in multiple, functionally interrelated proteins. Accordingly, determining the role of S-nitrosylation in health and disease requires methods for identification and quantitation of S-nitrosothiols in protein, as well as the specific Cys residues that are the targets of S-nitrosylation.

The biotin switch technique (BST) has been widely adopted for assaying protein S-nitrosylation. However, the BST is labor intensive and is characterized by relatively low throughput, and thus is not well suited for proteomic analysis of S-nitrosothiols in protein. Furthermore, the BST is not easily adapted to modern proteomic techniques, such as isotopic labeling.

Accordingly, it is desirable to develop a means for the identification and quantitation of specific protein modifications that requires a minimum number of steps, is more economical than previously used methods, more efficiently detects higher molecular weight modified proteins, and is more easily combined with mass spectrometric methods.

SUMMARY OF THE INVENTION

It has been discovered herein that a solid-phase thiol-reactive agarose-based matrix provides for an improved method of identifying thiol-based protein modifications.

One embodiment of the invention herein, denoted the first embodiment, is directed to a compound for the efficient solid-phase immobilization of post-translationally modified protein/peptide cysteine residues. The compound has one of the following general formulas:

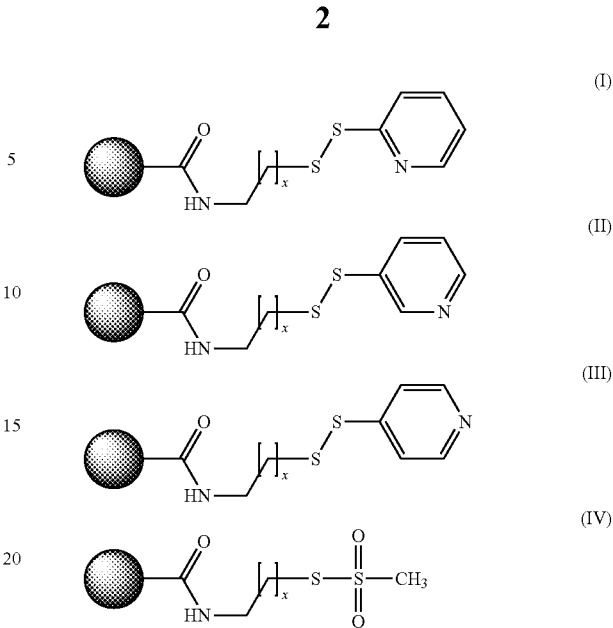

wherein ⬤ may be a solid-phase resin, such as agarose or an agarose-derived polymer support, and x may be an integer between 1 and 10.

Another embodiment of the invention herein, denoted the second embodiment, is directed to a method of synthesizing the 2-, 3- or 4-pyridyl disulfide versions of the compound of the first embodiment (i.e. compounds (I), (II), and (III)). The method generally comprises the steps of (i) reacting an amino-reactive resin with an alkyl compound comprising a primary amino group and a primary disulfide group to produce a resin bound disulfide, (ii) reducing the resin bound primary disulfide to a primary thiol and (iii) reacting the resin bound thiol with 2-, 3- or 4-pyridyl disulfide.

Another embodiment of the invention herein, denoted the third embodiment, is directed to a method of synthesizing the methylthiosulfonate version of the compound of the first embodiment (i.e. compound (IV)). The method generally comprises the step of reacting an amino-reactive resin with an amine-containing methylthiosulfonate.

Another embodiment of the invention herein, denoted the fourth embodiment, is directed to immobilizing a post-translationally modified protein/peptide to a compound of the first embodiment. The method generally comprises the step of conjugating the post-translationally modified protein/peptide to a compound of the first embodiment. Steps performed prior to conjugation may include (i) converting cysteine thiols of the post-translationally modified protein/peptide to either thio ethers or disulfides and (ii) liberating free thiols from previously modified protein/peptide cysteine thiols of the post-translationally modified protein/peptide.

Yet another embodiment of the invention herein, denoted the fifth embodiment, is directed to determining the presence and kind of any post-translational modification of cysteine in proteins or peptides cleaved therefrom and optionally for determining the location in a protein/peptide where modification has occurred, where reliance is placed on the immobilization of the fourth embodiment.

DETAILED DESCRIPTION

In the first embodiment of the present invention, a compound for the efficient solid-phase immobilization of post-translationally modified protein/peptide cysteine residues is described. The compound has one of the following general formulas:

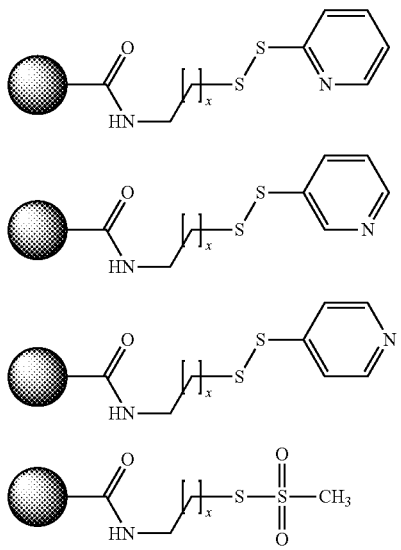

In the above formulas, ⬤ may be a solid-phase resin. Resins suitable for use in the first embodiment may generally be described as a polymeric support. Examples of these solid-phase resins include, but are not limited to, agarose, polyethylene glycol, dextrose, dextran and acrylamide and polymeric supports derived therefrom. In a specific aspect of the first embodiment, the resin is Sepharose™. Sepharose™ is available from Amersham Bioscience, Piscataway, N.J. Sepharose™ describes a cross-linked, beaded form of agarose, which is a polysaccharide polymer material extracted from seaweed.

Furthermore, in the above formula, x may be an integer between 1 and 10.

The compounds of the first embodiment are useful for immobilization of cysteine/thiol groups on proteins, peptides or other small molecules. The compounds of the first embodiment are considerably more reactive than other commercially available thiol/cysteine-reactive resins. The observed increased reactivity of the compounds of the first embodiment is attributable to decreased steric hindrance near the disulfide group, and complete lack of ionic character to marked increase in reactivity of 4-pyridyl disulfide and methylthiosulfonate has been noted relative to 2-pyridyl disulfide.

In the second embodiment of the present invention, a method for synthesizing the 2-, 3-, or 4-pyridyl disulfide version of the compound of the first embodiment (compounds (I), (II), (III) is disclosed. The method generally comprises the steps of (i) reacting an amino-reactive resin with an alkyl compound comprising a primary amino group and a primary disulfide group to produce a resin bound disulfide, (ii) reducing the resin bound primary disulfide to a primary thiol and (iii) reacting the resin bound thiol with 2-, 3- or 4-pyridyl disulfide.

As described above, the resin generally comprises a polymeric support, such as agarose. In a preferred aspect of the second embodiment, the starting resin material is Sepharose™-4B-NHS, available from Amersham Bioscience. NHS refers to N-hydroxysuccinimide, and the starting resin material may generally be illustrated as:

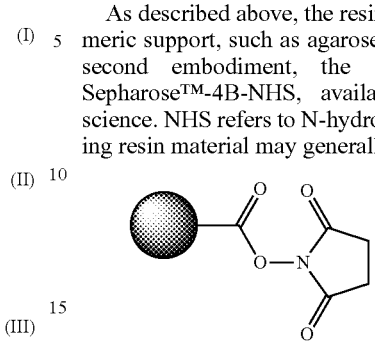

wherein the ⬤ is a solid-phase resin as described above. A specific example of the solid phase resin is Sepharose™-4B.

In the first step of the method of second embodiment, the resin is reacted with an alkyl compound comprising both a primary amino acid group and a primary disulfide group. The alkyl compound preferably has the formula $$H_2N-(CH_2)_x-S-S-(CH_2)_x-NH_2$$

wherein x may be an integer from 1 to 10. The alkyl compound is used in amount of 10 to 100 mM (2 ml alkyl compound per 1 ml of resin)

In addition to an alkyl compound comprising both a primary amino acid group and a primary disulfide group as described above, other suitable compounds may be reacted with the resin. For example, polyethylene glycol may be reacted with the resin.

In experiments supporting the invention, NHS is removed from Sepharose-4B-NHS and an amide bond is formed between the resin and the alkyl compound. The reaction between the resin and the alkyl compound preferably takes place in 100 mM sodium phosphate pH 8.0 for 12 hours at room temperature, followed by addition of 0.5 M ethanolamine.

In the second step, the resin bound disulfide is reduced with 100 mM dithiothreitol (DTT) and washed with >100 volumes of methanol.

In the third step, the resulting resin bound thiol is reacted with 2-, 3- or 4-pyridyl disulfide. The reaction between the 2-, 3- or 4-pyridyl disulfide and the resin bound disulfide preferably takes place in pure methanol for 12 hours at room temperature in the dark. A 100 mM of 2-, 3- or 4-pyridyl disulfide is used.

The efficacy of each reaction may be assessed by treatment with dithio-bis-nitrobenzoic acid (DTNB) to verify no remaining free thiol, and with DTT to determine the degree of 2-, 3- or 4-pyridyl disulfide content (for 2-PDS, $\epsilon_{343}$=8.08 mM$^{-1}$ cm$^{-1}$ and for 4-PDS, $\epsilon_{324}$=19.8 mM$^{-1}$ cm$^{-1}$). Resin capacity should be 4-6 μmol/ml resin.

The reaction is depicted in the following reaction scheme

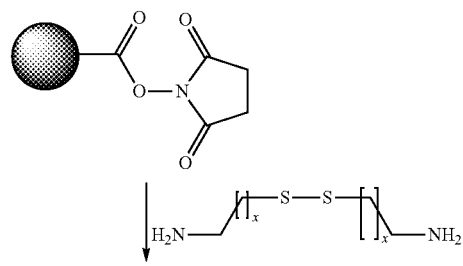

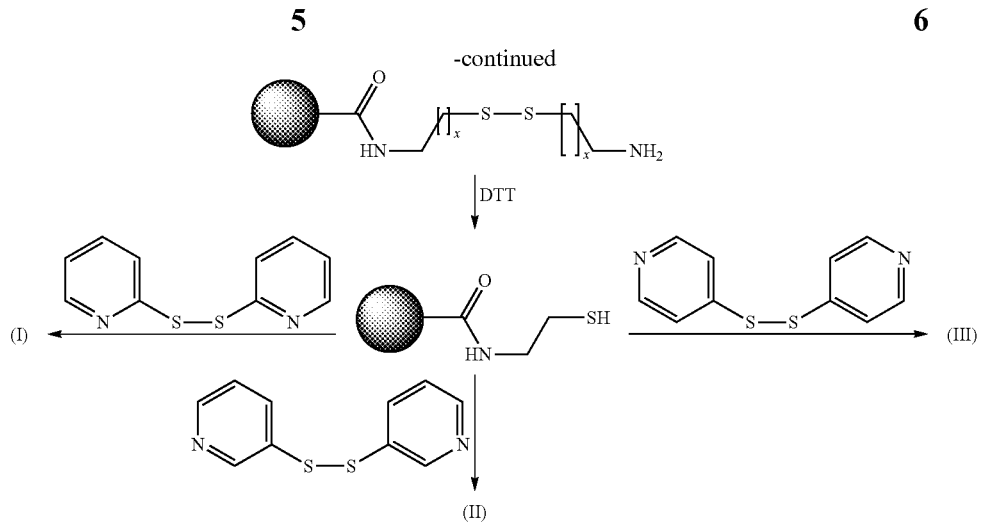

As shown in the reaction scheme depicted above, an intermediate step is performed between the first and third steps, where the disulfide bond in the alkyl compound is reduced. In this manner, half of the alkyl compound washes away and a new thiol group is provided which can react with the 2-, 3- or 4-pyridyl disulfide to form a new disulfide. The reducing agent used to reduce the disulfide in the alkyl compound may be any suitable reducing agent, for example, dithiothreitol (DTT).

In a third embodiment of the present invention, a method of synthesizing the methylthiosulfonate version of the compound of the first embodiment is provided. The method generally comprises reacting a resin with a methylthiosulfonate containing a primary amino group. A general method of synthesizing compound (IV) is illustrated below.

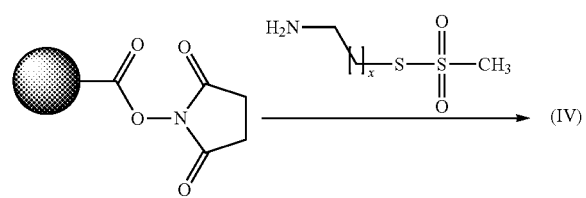

The resin used to synthesize the methylthiosulfonate version of the compound (i.e. compound IV) of the first embodiment is identical to the resin described above with respect to the second embodiment.

In a specific example, the methylthiosulfonate version of the compound (i.e. compound IV) is synthesized by allowing Sepharose-4B-NHS (Amersham Biosciences) to react with a 50-fold excess of mM 2-aminoethyl methanethiosulfonate in dimethylformamide solvent for 12 h at room temperature, followed by addition of 0.5 M ethanolamine. Following amide bond formation, the resin is washed repeatedly with dimethylformamide and stored in either dimethylformamide or isopropanol. Resin capacity is measured by a 5,5'-dithio-bis-(2-nitrobenzoic acid) (DTNB) assay.

In a fourth embodiment of the present invention, a method of immobilizing a post-translationally modified protein/peptide to a reactive solid phase matrix is provided. The method generally comprises conjugating a protein/peptide having undergone a post-translational thiol-based modification to the compound of the first embodiment.

The post-translationally modified protein/peptide is immobilized to the reactive solid-phase disulfide by way of a covalent bond. The post-translationally modified protein/peptide undergoes preparation steps to facilitate the formation of the covalent bond.

Firstly, cysteine thiols present in the post-translationally modified protein/peptide must be converted to either thioethers or disulfides. This conversion essentially serves as a block so that the thiols present in the post-translationally modified protein do not covalently bond to the solid-phase reactive disulfide and result in the measurement of a false positive (i.e., a thiol that did not undergo thiol-based modification such as S-nitrosylation). For conversion of thiols to thioethers, an alkylating agent may be used. Preferred alkylating agents include N-ethylmalemide (NEM), iodoacetamide and iodoacetic acid. For conversion of thiols to disulfides, a methylthiolating agent may be used. A preferred methylthiolating agent is S-methylmethanethiosulfonate. (MMTS)

Secondly, those thiols that have previously undergone thiol-based modification, such as S-nitrosylation, are liberated. The liberating agent (z) may vary depending on the type of thiol-based modification that is being identified. When the modification has resulted in S-acyl groups (thioesters), hydroxylamine, e.g. in an amount of 200 mM, is used to liberate the previously modified thiol. When the modification has resulted in S-nitrosothiol, ascorbate, e.g. in amount of 20 mM, is used to liberate the previously modified thiol. When the modification has resulted in sulfenic acid, aresenite, e.g. in amount of 10 mM, is used to liberate the previously modified thiol. When the modification has resulted in disulfides, dithiothreitol e.g. in amount of 10 mM, is used to liberate the previously modified thiol. It is therefore evident that the invention disclosed herein may be adapted to study numerous thiol-based modifications, including S-palmitoylation. The amounts of liberating agent recited are per 1-2 mg protein.

Having now freed the previously modified thiol, the post-translationally modified protein/peptide is free to conjugate with a compound of the first embodiment.

The reaction scheme for the forth embodiment is depicted below.

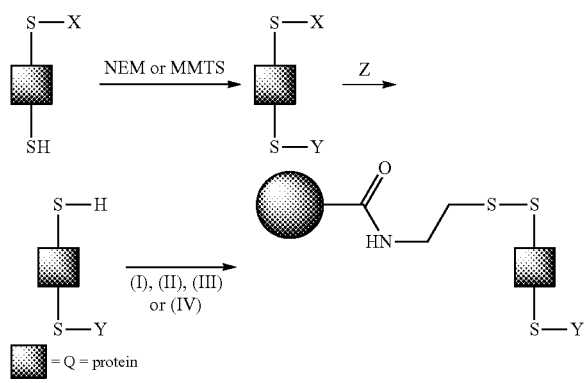

where Q is modified protein, X is modifying group on cysteine, SH is free thiol, Y is blocking group derived from NEM or MMTS and Z is liberating agent.

Once the post-translationally modified protein/peptide has been immobilized, various identification and quantitation methods may be applied. For example, the solid-phase immobilized protein may be eluted with beta-mercaptoethanol followed by polyacrylamide electrophoresis with silver staining or immunodetection. The bound proteins/peptides may also undergo proteolysis followed by elution of cysteine-bound peptides and identification by liquid chromatography and mass spectrometry.

The identification and quantification methods are illustrated by the fifth embodiment herein.

The fifth embodiment herein is directed to a method for determining the presence and kind of cysteine modification in a post-translationally modified protein/peptide which comprises the steps of (a) converting any cysteine thiols present in the protein/peptide to thioethers or disulfides which are blocking groups to provide blocked cysteine thiol group protein/peptide (b) admixing product of step (a) with a solid phase immobilizing resin compound of the first embodiment, e.g. 50 microliters of resin slurry (approximately 500 nmol of "binding capacity) per 1-2 mg protein (c) converting any cysteine modifying groups that are present in the blocked protein/peptide of step (a) to free thiol and conjugating blocked protein/peptide to said free thiol to immobilize the blocked protein/peptide.

(d) eluting the product of step (c) with reducing agent to remove resin constituting said solid phase.

(e) detecting whether or not protein/peptide is present

The detection of presence of protein/peptide in step (e) indicates the presence of post translational modification. The liberating agent (z) used for immobilization correlates with the kind of modifying group.

The detection can be by polyacrylamide gel electrophoresis (PAGE) with silver straining or by a reaction with antibody and western blotting.

The immobilizing can be followed by conjugating fluorophore to the immobilized protein/peptide to allow visualizing of protein/peptide bands in gel obtained in PAGE.

The immobilized protein can be digested with trypsin to cleave the protein/peptide into peptides which can be isolated to allow detection of location in protein/peptide of cysteine modification.

The invention is illustrated by the following Examples

Example 1

Preparation of (I), (II) and (III)

The solid-phase reactive disulfides are synthesized by allowing Sepharose™-4B-NHS (Amersham Biosciences) to react with an alkyl compound with both amino and disulfide groups of the formula $(H_2N-(CH_2)_x-SS-(CH_2)_x-NH_2)$ in 100 mM sodium phosphate pH 8.0 for 12 h at room temperature, followed by addition of 0.5 M ethanolamine. Following amide bond formation, the resin is treated with 100 mM dithiothreitol to fully reduce the resin-bound disulfide and washed repeatedly with water and methanol. In pure methanol, a solution containing 100 mM of 2-, 3- or 4-pyridyl disulfide is added for 12 h at room temperature in the dark. The resin is again washed and stored in isopropanol.

Example II

Preparation of III

To a slurry of Sepharose™ 4B-NHS (Amersham. Biosciences) was added 5 volumes of 50 mM cystamine in 100 mM phosphate pH 8.0. Following rotation for 12 h at 25° C., the resin was treated with 0.5 M ethanolamine and thoroughly washed with 100 mM phosphate pH 8.0, $H_2O$, and MeOH. The resin was reduced with 10 volumes of 100 mM DTT in 50 mM phosphate pH 8.0, then thoroughly washed with 100 mM phosphate pH 8.0, followed by MeOH. Between 4 and 8 volumes of 100 mM 4-pyridyl disulfide (PDS) in MeOH was then added to the resin, followed by rotation at 4° C. for 12 h in the dark. The resin was washed repeatedly with MeOh, $H_2O$ and finally isopropanol, then stored at 4° C. in the dark. Total binding capacity was determined by treating a small portion of the resin with DTT, followed by measuring the absorbance of 2-thiopyridone at 343 nm ($\epsilon=8.08$ $mM^{-1}$).

Example III

Preparation of (IV)

To 1 ml of Sepharose-NHS (sepharose functionalized with N-hydroxysuccinimide groups) is added a final concentration of 10 mM 2-aminoethyl methylthiosulfonate hydrobromide (MTSEA, HBr) in 10 ml of dimethylformamide (DMF) solvent. The reaction is rotated at room temperature for 18 hour, washed extensively in DMF and stored at 4° C. in DMF. The resin is stable for at least 2 months under these conditions.

Example IV

Isolation of S-Nitrosylated Proteins by Resin Immobilization (SNO-RAC)

The cellular lysate or material of interest (from murine macrophages, *E. Coli* subjected to nitrosative stress, S-nitrosylated glycerol-3-phosphate-dehydrogenase (GPDH) on S-nitrosylated peroxiredoxin-1) (1 mg cellular lysate or protein) is mixed into 2 ml of HEN buffer containing a final concentration of 0.1% MMTS and 2.5% SDS. This "blocking" reaction is incubated at 50° C. for 20 min and proteins are precipitated following the addition of 3 volumes (6 ml) of cold acetone. After incubation at −20° C. for 20 min, the mixture is centrifuged at 2000 g for 5 min. The white protein pellet is washed repeatedly with 70% acetone and resuspended in 240 µl of HENS buffer (HEN+1% SDS) per 1 mg of protein. To this material is added 30 µl of the thiol-reactive resin (either 2-, 3-, 4-PDS or methylthiosulfonate resin) per 1 mg of protein. Sodium ascorbate is added to a final concentration of 20 mM and the reaction is rotated at room temperature in the dark for 3-12 h. The resin is then washed repeatedly with HENS buffer and the isolated proteins are eluted with 60 µl of HENS/10 buffer (HEN diluted 1:10 in $H_2O$, containing 2% SDS) containing 1% 2-mercaptoethanol. The eluted proteins are then resolved by SDS-PAGE and visualized either directly (e.g. silver or coomassie staining of the gel) or indirectly via western blotting with an antibody against the proteins of interest.

Example V

Isolation of S-Acylated Proteins by Resin Immobilization (ACYL-RAC)

The cellular lysate or material of interest is (bovine brain membranes) (2 mg. protein) is mixed into 2 ml of HEN buffer containing a final concentration of 0.1% MMTS and 2.5% SDS. This "blocking" reaction is incubated at 50° C. for 20 min and proteins are precipitated following the addition of 3 volumes (6 ml) of cold acetone. After incubation at −20° C. for 20 min, the mixture is centrifuged at 2000 g for 5 min. The white protein pellet is washed repeatedly with 70% acetone and resuspended in 240 µl of HENS buffer (HEN+1% SDS) per 1 mg of protein. To this material is added 30 µl of the thiol-reactive resin (either 2-, 3-, 4-PDS or methylthiosulfonate resin) per 1 mg of protein. Neutral hydroxylamine is added to a final concentration of 200 mM and the reaction is rotated at room temperature in the dark for 3-12 h. The resin is then washed repeatedly with HENS buffer and the isolated proteins are eluted with 60 µl of HENS/10 buffer (HEN diluted 1:10 in $H_2O$, containing 2% SDS) containing 1% 2-mercaptoethanol. The eluted proteins are then resolved by SDS-PAGE and visualized either directly (e.g. silver or coomassie staining of the gel) or indirectly via western blotting with an antibody against the proteins of interest.

Example VI

Isolation of Sulfenic Acid-Oxidized Proteins by Resin Immobilization

The cellular lysate or material of interest (1-2 mg of protein) is mixed into 2 ml of HEN buffer containing a final concentration of 0.1% MMTS and 2.5% SDS. This "blocking" reaction is incubated at 50° C. for 20 min and proteins are precipitated following the addition of 3 volumes (6 ml) of cold acetone. After incubation at −20° C. for 20 min, the mixture is centrifuged at 2000 g for 5 min. The white protein pellet is washed repeatedly with 70% acetone and resuspended in 240 µl of HENS buffer (HEN+1% SDS) per 1 mg of protein. To this material is added 30 µl of the thiol-reactive resin (either 2-, 3-, 4-PDS or methylthiosulfonate resin) per 1 mg of protein. Sodium arsenite is added to a final concentration of 20 mM and the reaction is rotated at room temperature in the dark for 3-12 h. The resin is then washed repeatedly with HENS buffer and the isolated proteins are eluted with 60 µl of HENS/10 buffer (HEN diluted 1:10 in $H_2O$, containing 2% SDS) containing 1% 2-mercaptoethanol. The eluted proteins are then resolved by SDS-PAGE and visualized either directly (e.g. silver or coomassie staining of the gel) or indirectly via western blotting with an antibody against the proteins of interest.

Example VII

Isolation of Disulfide-Oxidized Proteins by Resin Immobilization

The cellular lysate or material of interest (1-2 mg of protein) is mixed into 2 ml of HEN buffer containing a final concentration of 20 mM N-ethylmaleimide (NEM) and 2.5% SDS [importantly, this protocol requires S-alkylation for this "blocking" reaction, which is achieved with NEM. Since this protocol employs a more reactive reductant (i.e. DTT) to remove disulfide groups, MMTS (as employed for S-acyl or SNO assays) is incompatible with this method as it is reversed by DTT]. This "blocking" reaction is incubated at 50° C. for 20 min and proteins are precipitated following the addition of 3 volumes (6 ml) of cold acetone. After incubation at −20° C. for 20 min, the mixture is centrifuged at 2000 g for 5 min. The white protein pellet is washed repeatedly with 70% acetone and resuspended in 240 µl of HENS buffer per 1 mg of protein (HEN+1% SDS). To this material is added a final concentration of 20 mM DTT for 1 hour at room temperature. To remove excess DTT, 3 volumes of acetone are again added, the mixture is incubated at −20° C. for 20 min and centrifuged at 2000 g for 5 min. The white pellet is washed repeatedly with 70% acetone and resuspended in 240 µl of HENS buffer per 1 mg of protein. To this material is added 30 µl of the thiol-reactive resin (either 2-, 3-, 4-PDS or methylthiosulfonate resin) per 1 mg of protein, and the reaction is rotated at room temperature in the dark for 3-12 h. The resin is then washed repeatedly with HENS buffer and the isolated proteins are eluted with 60 µl of HENS/10 buffer (HEN diluted 1:10 in $H_2O$, containing 2% SDS) containing 1% 2-mercaptoethanol. The eluted proteins are then resolved by SDS-PAGE and visualized either directly (e.g. silver or coomassie staining of the gel) or indirectly via western blotting with an antibody against the proteins of interest.

Example VIII

On-Resin Labelling of Proteins with Fluorescent Compounds

Prior to elution from the resin, proteins may be "tagged" with chemical compounds bearing one group that reacts with proteins and another group that is fluorescent. A popular reagent for serving such a purpose are the "Cy" dyes (e.g. Cy3, Cy5). To employ this approach for protein visualization, resin-bound proteins may be directly "tagged" via an "on-resin" approach, which is advantageous since excess compound is readily removed by washing, whereas most other protocols require a complicated removal step.

The cellular lysate or material of interest (1-2 mg of protein) is subjected to blocking reaction as described in Example VI: To the blocked material in HENS buffer was added compound (I), (II), (III) or (IV) (50 µl resin slurry per milligram protein) (50 µl is approximately 500 nmol binding capacity) in the presence or absence of neutral hydroxylamine (final 200 mM). Following rotation in the dark for 2-4 hr., the resin was wasted with 4×1 ml HENS buffer, then 2×1 ml HENS/10 buffer (HENS diluted 1:10).

For Cy3 or Cy5 labeling, resins containing bound proteins were equilibrated in 1 ml of 100 mM sodium borate pH 8.5, followed by addition of 5 µl Cy3- or Cy5-NHS (GE Life Sciences, 1 mM in DMSO), and rotated at RT in the dark for 1 h. These "Cy-tagged" proteins are washed extensively with 100 mM sodium borate and HENS buffer, and eluted with 60 μl HEN/10 containing 1% mM 2-mercaptoethanol for 20 min at RT, and 40 μl each eluant was used for SDS-PAGE. S-acylated proteins were detected by Acyl-RAC (described above) combined with Cy5-labeling as described.

Example IX

Mapping of CYS-Modified-Sites by on-Resin Trypsinization and LC-MS/MS

Once Cys-modified proteins are covalently bound ("immobilized") on the resin, the specific site of modification (i.e. Cys-residue) can be isolated by proteolytically digesting the resin-bound proteins, washing away all unbound material, and eluting the remaining peptides with reductant. By this route, one may isolate peptides that contain each Cys residue that has undergone the modification of interest (e.g. SNO, acyl, oxidation). The identification of these sites is determined by mass spectrometry, whereby the exact masses of each peptide (and peptides fragments thereof) are measured and statistically fit to a database of expected peptide masses. Peptides bearing an "observed" mass that is very similar to the "expected" mass are considered positive identifications, and therefore the specific Cys site can be determined. In an experiment carried out, a peptide containing Cys53 of UbcH7 was isolated, demonstrating that this Cys residue undergoes modification to SNO within intact mouse cells (macrophages).

Following protein (cellular lysate or material of interest) immobilization as described, resins are washed with 10 mM ammonium bicarbonate ($NH_4HCO_3$), and 10 μg of sequencing grade trypsin in 1 ml 10 mM $NH_4HCO_3$ is added to the resin. Following rotation at 37° C. for 8 h, the resin is washed with 10 mM $NH_4HCO_3$ (4×1 ml), HENS buffer (4×1 ml) and 10 mM $NH_4HCO_3$ (4×1 ml). When indicated, samples were then acetylated with 5 μl $H_6$- or $D_6$-acetic anhydride in 1 ml of 100 mM sodium phosphate pH 8.0, and rotated for 30 min. Following extensive washing with 5×1 ml HENS/10 and 5×1 ml 10 mM $NH_4HCO_3$, samples are eluted for 30 min in 200 μl 10 mM $NH_4HCO_3$ with 10 mM DTT. The eluant was removed, beads were rinsed with 400 μl $dH_2O$, and these two fractions were combined, passed through a 0.45 μm filter and concentrated by speedvac.

This material bears peptides that contain the specific Cys-modified residues, which are identified by liquid chromatography and tandem mass spectrometry (LC-MS/MS). The LC chromatogram shows that more peptides are obtained from a sample that contains high levels of SNO (compared to an untreated sample). These peptides are then identified by mass spectrometry, as frequently employed by many laboratories.

Variations

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:

1. A method of immobilizing an S-nitrosylated protein or peptide to a reactive solid-phase matrix comprising a compound of the following formula (I), (II), (III), or (IV), as shown respectively:

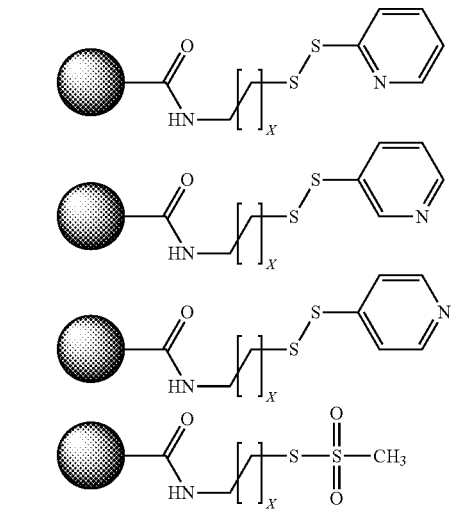

wherein ● is a solid-phase resin and x is an integer between 1 and 10, and wherein said method comprises:
(a) obtaining a sample comprising an S-nitrosylated protein or peptide;
(b) converting any cysteine thiols present in the S-nitrosylated protein or peptide to thioethers or disulfides by treating the sample with an alkylating agent or a methylthiolating agent, respectively;
(c) removing the S-nitrosylated thiols present in the S-nitrosylated protein or peptide from the protein or peptide by treating the sample with ascorbate; and
(d) conjugating the protein or peptide to a compound of formula (I), (II), (III) or (IV) by mixing the sample with the reactive solid-phase matrix.

2. The method of claim 1, wherein the alkylating agent is selected from the group consisting of N-ethylmalemide, iodoacetamide and iodoacetic acid; and the methylthiolating agent is S-methylmethanethiosulfonate.

3. The method of claim 1, wherein the solid-phase resin is agarose or a polymeric support comprising agarose.

4. The method of claim 1, further comprising the following steps (e) and (f):
(e) eluting the protein or peptide from the reactive solid-phase matrix by treating the conjugated protein or peptide with a reducing agent; and
(f) detecting the presence of the protein or peptide in the eluate.

* * * * *